US010288538B2

(12) United States Patent
Mozsgai et al.

(10) Patent No.: US 10,288,538 B2
(45) Date of Patent: May 14, 2019

(54) NON-DESTRUCTIVE EVALUATION OF CORDAGE PRODUCTS

(71) Applicant: SAMSON ROPE TECHNOLOGIES, Ferndale, WA (US)

(72) Inventors: Greg Zoltan Mozsgai, Ferndale, WA (US); James R. Plaia, Ferndale, WA (US); Chia-Te Chou, Ferndale, WA (US)

(73) Assignee: SAMSON ROPE TECHNOLOGIES, Ferndale, WA (US)

( * ) Notice: Subject to any disclaimer, the term of this patent is extended or adjusted under 35 U.S.C. 154(b) by 120 days.

(21) Appl. No.: 15/282,033

(22) Filed: Sep. 30, 2016

(65) Prior Publication Data

US 2017/0089817 A1   Mar. 30, 2017

Related U.S. Application Data

(60) Provisional application No. 62/235,263, filed on Sep. 30, 2015, provisional application No. 62/262,622, filed on Dec. 3, 2015.

(51) Int. Cl.
*G01N 3/06* (2006.01)
*G01N 3/08* (2006.01)

(52) U.S. Cl.
CPC .............. *G01N 3/08* (2013.01); *G01N 3/066* (2013.01); *G01N 2203/028* (2013.01); *G01N 2203/0244* (2013.01)

(58) Field of Classification Search
None
See application file for complete search history.

(56) References Cited

U.S. PATENT DOCUMENTS

| 3,653,258 A | 4/1972 | King |
| 4,803,888 A | 2/1989 | Choquet |
| 4,979,125 A * | 12/1990 | Kwun ............... B65H 63/06 702/35 |

(Continued)

FOREIGN PATENT DOCUMENTS

| CN | 201173836 Y | 12/2008 |
| CN | 101776552 A | 7/2010 |

(Continued)

OTHER PUBLICATIONS

Supratik, Data; Computing Stiffness of Linear Elastic Structures: Part 1; 2014, Apr. 3; p. 1-8.*

(Continued)

*Primary Examiner* — Andrew Schechter
*Assistant Examiner* — Terence E Stifter, Jr.
(74) *Attorney, Agent, or Firm* — BakerHostetler (57) ABSTRACT

A method for non-destructively estimating a current physical condition of a cordage product in-service is described. The method involves obtaining sensor data associated with the cordage product while in-service handling a load. The sensor data includes any combination of cordage product elongation data, applied load data, and diametric data. The method further includes determining an axial stiffness value associated with the cordage product based on the sensor data and estimating a health state of the cordage product based on the determined axial stiffness value. The estimated health state is indicative of the current physical condition of the cordage product.

22 Claims, 5 Drawing Sheets

(56) References Cited

U.S. PATENT DOCUMENTS

| | | | |
|---|---|---|---|
| 4,987,030 A * | 1/1991 | Saito | D01F 8/12 |
| | | | 264/172.15 |
| 5,251,492 A | 10/1993 | Nowag | |
| 5,821,430 A | 10/1998 | Kwun et al. | |
| 6,123,176 A | 9/2000 | O'Donnell et al. | |
| 6,923,065 B2 | 8/2005 | Smith et al. | |
| 6,999,641 B2 | 2/2006 | Williams et al. | |
| 7,117,981 B2 | 10/2006 | Logan et al. | |
| 7,123,030 B2 | 10/2006 | Robar et al. | |
| 7,752,830 B2 | 7/2010 | Goldwater et al. | |
| 8,240,200 B2 | 8/2012 | Chocron et al. | |
| 2003/0111298 A1 | 6/2003 | Logan et al. | |
| 2005/0231207 A1* | 10/2005 | Goldwater | D02G 3/441 |
| | | | 324/522 |
| 2006/0213175 A1* | 9/2006 | Smith | B66B 7/06 |
| | | | 57/237 |
| 2007/0113640 A1 | 5/2007 | De Jesus et al. | |
| 2008/0190217 A1 | 8/2008 | Laurent et al. | |
| 2010/0084223 A1 | 4/2010 | Fargo et al. | |
| 2011/0268313 A1 | 11/2011 | Winter et al. | |
| 2014/0027401 A1* | 1/2014 | Ilaka | B66C 13/16 |
| | | | 212/276 |
| 2014/0109682 A1 | 4/2014 | Mupdende et al. | |
| 2014/0197829 A1 | 7/2014 | Szielasko et al. | |
| 2014/0266169 A1* | 9/2014 | Huntley | G01D 1/00 |
| | | | 324/222 |

FOREIGN PATENT DOCUMENTS

| | | | |
|---|---|---|---|
| CN | 102359840 A | | 2/2012 |
| JP | H09-043283 A | | 2/1997 |
| JP | H10-221049 A | | 8/1998 |
| JP | H10-318741 A | | 12/1998 |
| JP | 2005-512921 A | | 5/2005 |
| JP | 2008-533482 A | | 8/2008 |
| JP | 2011-247700 A | | 12/2011 |
| WO | WO 1989/004960 A1 | | 6/1989 |
| WO | WO 2002/046082 A1 | | 6/2002 |
| WO | WO 2007/145511 A1 | | 12/2007 |
| WO | WO 2015/175202 A1 | | 11/2015 |
| WO | WO 2017/059365 A1 | | 4/2017 |

OTHER PUBLICATIONS

International Patent Application No. PCT/US2016/55009; Int'l Search Report and the Written Opinion; dated Jan. 19, 2017; 17 pages.
https://scholar.google.com/scholar?hl=en&as_sdt=0%2C48&q=tsukada%3B+study+on+non+destructive+testing+for+wire-rope%3B+1990&btnG=; Kazuhiko Tsukada; "Study on non-destructive testing for wire-rope deterioration"; Jan. 1990; p. 132-139—(English Summary Only).
European Patent Application No. 16852786.9; Extended Search Report; dated Sep. 14, 2018; 10 pages.

* cited by examiner

NON-DESTRUCTIVE EVALUATION OF CORDAGE PRODUCTS

CROSS REFERENCE TO RELATED APPLICATIONS

This application claims benefit under 35 U.S.C. § 119(e) of U.S. Provisional Application 62/235,263, filed Sep. 30, 2015, and U.S. Provisional Application 62/262,622, filed Dec. 3, 2015. The contents of each are incorporated herein by reference.

TECHNICAL FIELD

The disclosure relates generally, but not exclusively, to systems and methods for estimating a current physical condition of a cordage product while in-service through non-destructive evaluation.

BACKGROUND

Synthetic ropes and other cordage products are used in many industries for a variety of applications. For example, the maritime industry may use cordage products in mooring operations to secure a ship to a pier, whereas the construction industry may use cordage products with cranes to lift and transport heavy items. In each of these various applications, a load is applied to a cordage product that results in forces being exerted on the cordage product. How the cordage product reacts to those forces depends on tensile properties of the cordage product.

Prior to being placed in-service, a cordage product may conform to an initial load-elongation curve that characterizes various tensile properties of the cordage product. Examples of such tensile properties include modulus of elasticity, elastic limit, elongation, proportional limit, cross-sectional area reduction, tensile strength, yield point, yield strength, and the like. The initial load-elongation curve may provide a baseline indication of how the cordage product will react to an applied load.

However, when placed in-service, the cordage product is subjected to various loading and service conditions that change one or more aspects of the initial load-elongation curve. These loading and service conditions represent varying levels and/or modes of stress exerted on the cordage product, which degrade the cordage product's tensile properties over time. Such degradation is indicative of the cordage product's physical condition deteriorating, which renders the cordage product more susceptible to failure.

Several factors may contribute to this deterioration of the synthetic rope's physical condition. Examples of such factors include abrasion, cutting, fatigue, shock loading, twist buildup, environmental exposure, and the like. While some factors may be observed through tactile or visual inspection, the ultimate impact of the factors to the cordage product's physical condition is difficult to ascertain. Systems and methods for non-destructively evaluating a cordage product in-service over time are needed.

SUMMARY

Disclosed herein are methods, systems, and computer readable storage media that provide for estimating a current physical condition of a cordage product while in-service through non-destructive evaluation of an axial stiffness value of the cordage product. The disclosed techniques determine the axial stiffness value in real-time by monitoring sensor data associated with the cordage product as a load is applied. In some embodiments, the sensor data includes measurements of a tension exerted on the cordage product by the applied load. In some embodiments, the sensor data includes measurements of an elongation associated with the cordage product as the load is applied. In some embodiments, the disclosed techniques use reference data associated with the physical condition of the cordage product to determine the axial stiffness value. Examples of such reference data include an initial load-elongation curve, historical sensor data associated with the cordage product, and historical axial stiffness values determined using the historical sensor data. These and other features will be more clearly understood from the following detailed description taken in conjunction with the accompanying drawings and claims This Summary is provided to introduce a selection of concepts in a simplified form that are further described in greater detail below in the Detailed Description. This Summary is not intended to identify key features or essential features of the claimed subject matter, nor is it intended to limit the scope of the claimed subject matter.

DETAILED DESCRIPTION OF ILLUSTRATIVE EMBODIMENTS

Embodiments of the present disclosure provide systems, methods, and computer readable storage media for estimating a current physical condition of a cordage product while in-service through non-destructive evaluation of an axial stiffness value of the cordage product. The axial stiffness value may be determined, in part, by monitoring a tensile force exerted on a cordage product when a load is applied to the cordage product. Generally, when tensile force is applied to a cordage product in an axial direction, stress occurs in the cordage product, as does tensile strain proportional to the stress.

Figure 1:
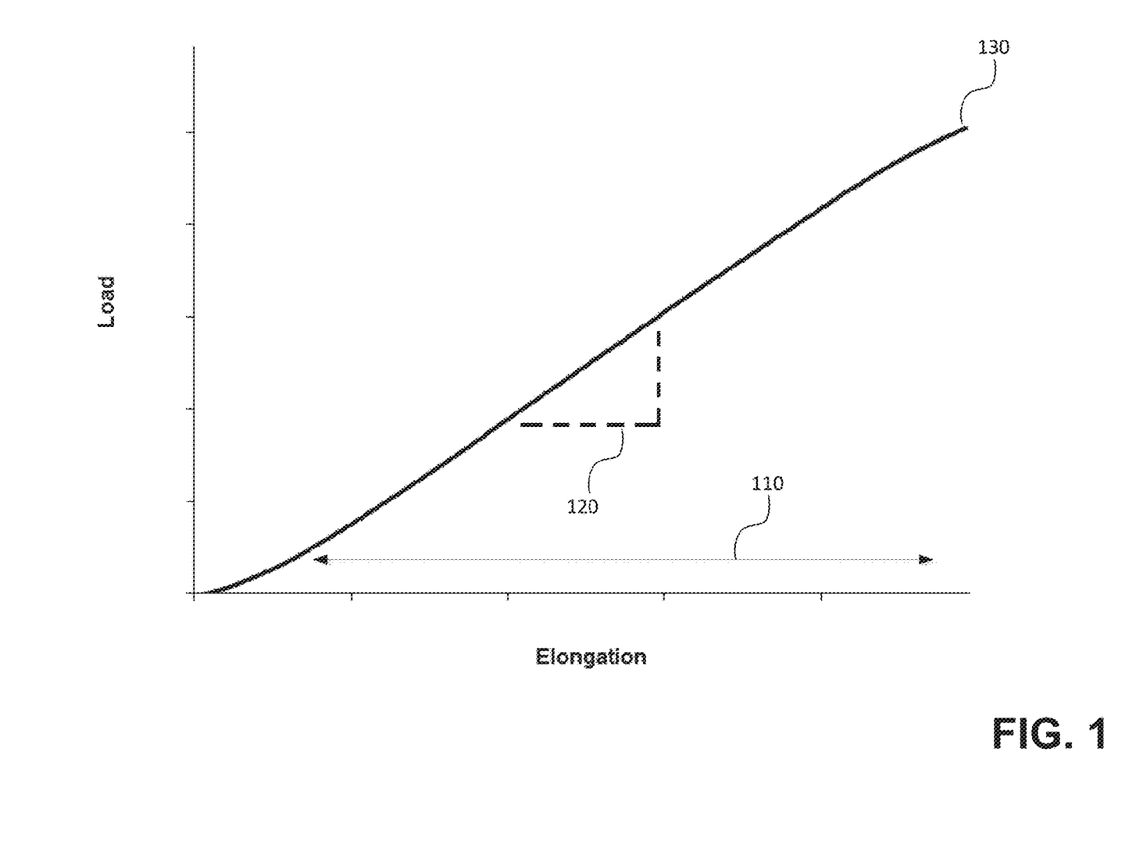
FIG. 1 is a graph illustrating a load-elongation curve, in accordance with an embodiment.

When a cordage product is subjected to this tensile strain, elongation occurs. Elongation refers to a behavior of the cordage product in which a length of the cordage product increases. In an embodiment, a cross-sectional area of the cordage product may also change as the length of the cordage product increased based on a Poisson ratio associated with the cordage product. The axial stiffness value may also be determined, in part, by monitoring an elongation of a cordage product when a load is applied to the cordage product. FIG. 1 depicts an example of a load-elongation curve 100 that characterizes various tensile properties of a cordage product. In FIG. 1, tensile force resulting from loads applied to a cordage product is plotted relative to elongation of the cordage product response to the applied loads. As shown by FIG. 1, load-elongation curve 100 includes an elastic region 110.

Elastic region 110 is a region of load-elongation curve 100 in which a linear relationship exists between a tensile force exerted on a cordage product by an applied load and an elongation resulting from the tensile force. As long as a cordage product remains in elastic region 110 while under stress the cordage product tends to behave elastically. In such a case, as tensile force increases, the cordage product deforms through elongation and tends to recover by returning to an undeformed state when the applied load is removed.

A slope 120 of elastic region 110 is referred to as a modulus of elasticity or Young's modulus of the cordage product. In an embodiment, slope 120 represents an axial stiffness of the cordage product that is independent of a length of the cordage product. At break point 130, a cordage product is no longer able to resist a tensile force exerted on the cordage product by an applied load. Accordingly, break point 130 represents a point of load-elongation curve 100 at which the cordage product may rupture, break, or otherwise fail.

Figure 2:
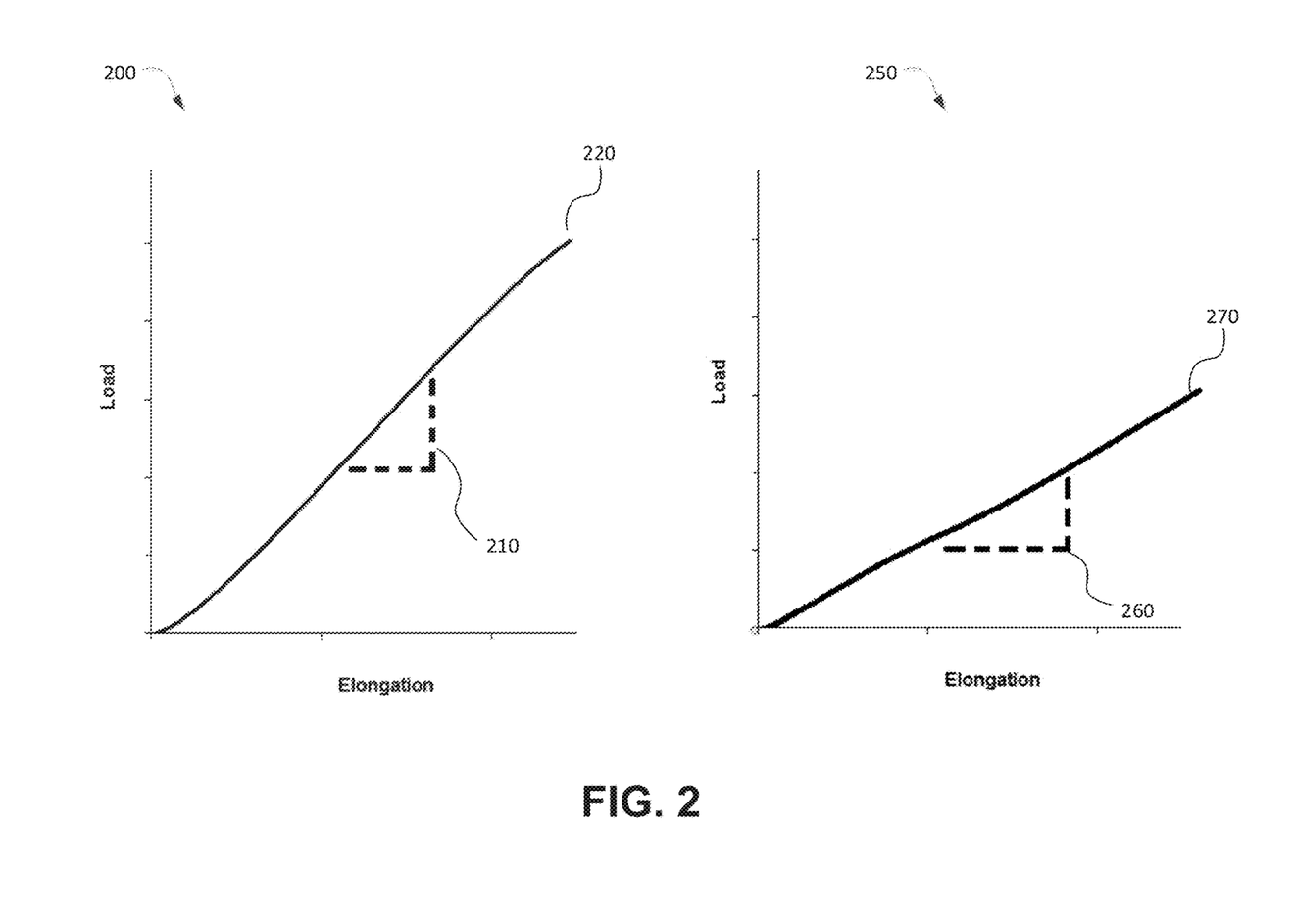
FIG. 2 is a graph comparing an initial load-elongation curve for a cordage product prior to being placed in-service with a subsequent load-elongation curve for the cordage product after being placed in-service, in accordance with an embodiment.

As discussed above, a cordage product may conform to an initial load-elongation curve characterizing various tensile properties of the cordage product prior to being placed in-service. In FIG. 2, this initial load-elongation curve is represented by curve 200. After being placed in-service, the cordage product is subjected to various loading and service conditions that degrade one or more tensile properties of the cordage product over time. Consequently, the cordage product may not conform to the initial load-elongation curve 200 after being placed in-service over a period of time.

Instead, the cordage product may conform to a subsequent load-elongation curve characterizing the various tensile properties of the cordage product after being placed in-service. In FIG. 2, this subsequent load-elongation curve is represented by curve 250. As illustrated by FIG. 2, the various loading and service conditions that degrade the tensile properties of the cordage product in-service also alter aspects of the cordage product's load-elongation curve. For example, an elastic stiffness of the cordage product may decline over time due to a decrease in cross-sectional area of the cordage product, a decrease in an elastic modulus of the cordage product, a combination of these decreases in cross-sectional area and elastic modulus, and the like. The decrease in cross-sectional area may come from physical damage, breakage, and/or removal of one or more fibers composing the cordage product. The decrease in the elastic modulus may be due to degradation of materials composing the one or more fibers, such as chain scission, recrystallization, and the like. And, even if a cordage product does continue to appear to conform to the initial load-elongation curve 200 despite being damaged, at some point in time in the future, the rate at which non-conformity may result accelerate, thereby causing the cordage product to suddenly conform to the load-elongation curve 250. Accordingly, it may be desirable to constantly monitor the cordage product while in-service so as to estimate its current physical condition.

One aspect that may be altered by the various loading and service conditions may include the cordage product's modulus of elasticity. For example, an initial modulus of elasticity 210 of initial load-elongation curve 200 is noticeably different than a subsequent modulus of elasticity 260 of subsequent load-elongation curve 250. Thus, the cordage product's elongation behavior in the elastic region changes after being placed in-service.

Another aspect that may be altered by the various loading and service conditions may include the cordage product's break point. For example, an initial break point 220 of initial load-elongation curve 200 may not be the same as a subsequent break point 270 of subsequent load-elongation curve 250. Therefore, the cordage product may rupture, break, or otherwise fail under a lower tensile load after being placed in-service than prior to being placed in-service. As such, monitoring tensile forces exerted on a cordage product and/or resulting elongation of the cordage product when loads are applied may provide for non-destructive evaluation of a current physical condition of the cordage product.

Figure 3:
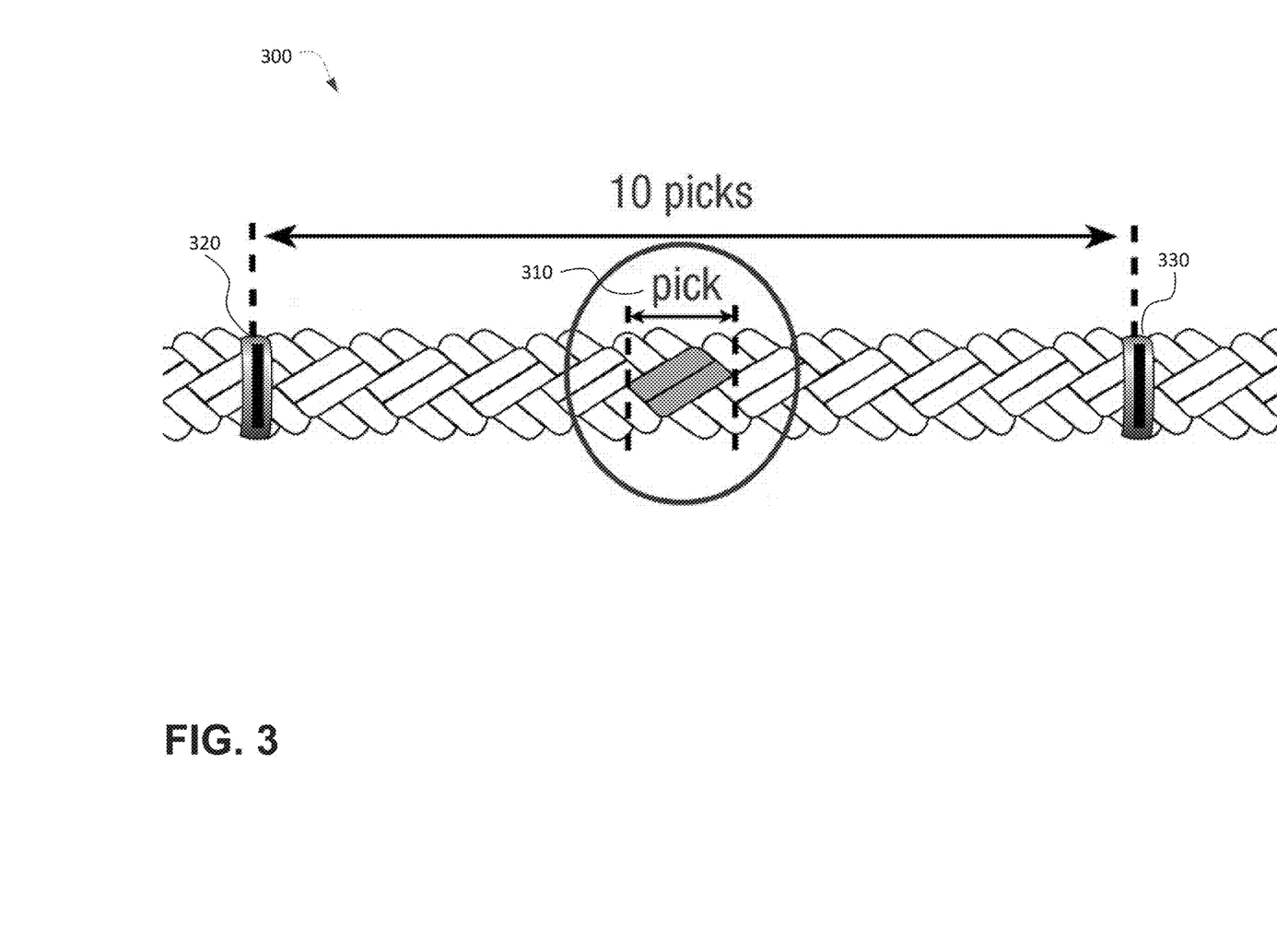
FIG. 3 illustrates an example of a fiber rope for implementing aspects of the present invention.

FIG. 3 provides an example of a cordage product with various tensile properties that may be characterized by the load-elongation curves described above. The example cordage product illustrated by FIG. 3 is fiber rope 300. While embodiments of the present disclosure are described in terms of a fiber rope, one skilled in the art will recognize that fiber rope 300 is but one example of a suitable cordage product for implementing aspects of the invention. Fiber rope 300 is composed of a plurality of fibers or filaments that are combined to form yarns (e.g., basic yarns, intermediate yarns, or rope yarns) that are then combined to form strands. The strands are then twisted, plaited, or braided to form fiber rope 300.

Each yarn may include natural fibers, synthetic fibers, or blends of natural and synthetic fibers. Natural fibers include cotton, sisal, wool, bamboo, flax, hemp, and the like. Synthetic fibers may include polyethylene terephthalate (PET), polypropylene, polyethylene, aramid, high-modulus polyethylene, (HMPE) or ultra-high molecular weight polyethylene (UHMWPE), nylon, polyester, liquid crystal polymer (LCP), carbon, glass, basalt, other organic and inorganic synthetic fibers.

Different types of fibers have different material properties that impact each type of fiber and each type of fiber includes a large range of grades, which can each possess very different material properties. These different material properties may in turn affect one or more tensile properties (e.g., moduli of elasticity, strength, weight, and creep characteristics) of fiber rope 300. Accordingly, some embodiments of the present disclosure may utilize reference data that includes known information regarding the material properties of the fibers that compose fiber rope 300 in estimating a current physical condition of fiber rope 300.

In some embodiments, fiber rope 300 includes known features that facilitate in estimating a current physical condition of fiber rope 300. In an embodiment, a known distance (e.g., a gage length) may separate the two or more known features of fiber rope 300. In an embodiment, the known features may include pick 310 that represents either a single point (i.e., one end of the pick 310) or a matching set of points (i.e., both ends of the pick 310) at which individual strands composing fiber rope 300 crossover each other.

In an embodiment, the known features of fiber rope 300 may include marks 320 and 330. Marks 320 and 330 represent external markings applied to fiber rope 300 at predetermined positions. Examples of such external markings include particular fiber, yarn, or strand braid patterns, externally applied coating material additives, coloration changes, and the like. The coloration changes may be implemented using materials that are visibly distinguishable under standard lighting conditions or using materials that become perceivable when activated by electromagnetic radiation of a particular wavelength (e.g., ultraviolet or infrared). Reflective and fluorescing materials may also be used to implement the human or machine visible changes. In an embodiment, the known features may include embedded elements (not depicted) that are detectable externally through ultrasonic sensing, x-ray or terahertz imaging, computed tomography, and the like. The embedded elements may be implemented using metallic wire, metallic elements, or other fibrous elements that may be detected externally. Other pluralities of repeatable points (i.e., that can be monitored once and the same monitoring can then be repeated) on or in the fiber rope 300 may similarly be used to monitor the fiber rope 300 in accordance with the present disclosure.

Figure 4:
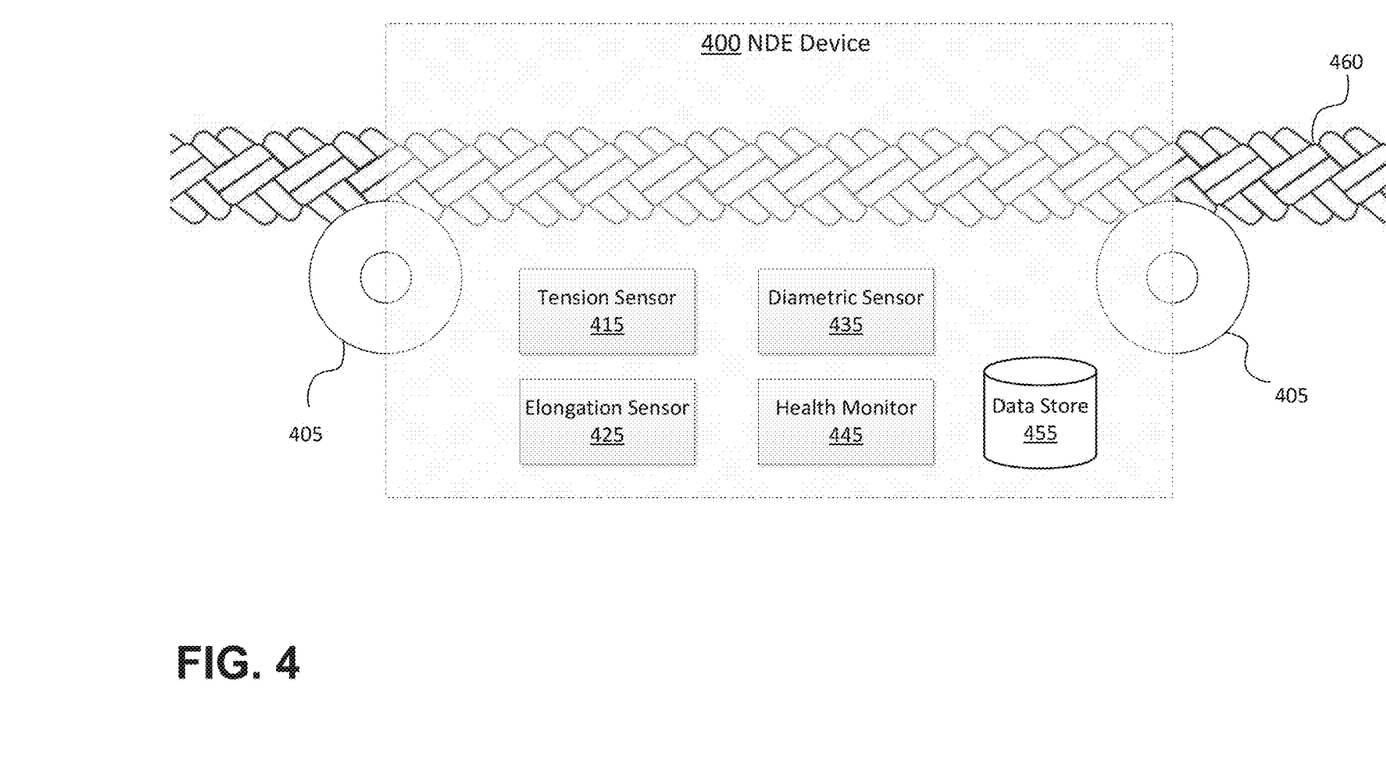
FIG. 4 depicts an example operational environment for implementing aspects of the present invention.

Turning to FIG. 4, a block diagram is illustrated showing a non-destructive evaluation (NDE) device 400 according to one embodiment of the present invention. NDE device 400 is depicted while performing a non-destructive evaluation of a cordage product 450 under a tensile load (not shown, but at either end of cordage product 450) after being placed in-service. In an embodiment, NDE device 400 remains stationary while cordage product 450 moves relative to NDE device 400. In an embodiment, cordage product 450 remains stationary while NDE device 400 moves relative to cordage product 450. The components shown in FIG. 4 are but a few of the components that embodiments of the present invention may interact with during operation. Accordingly, the components illustrated therein are described with an emphasis on their function, rather than their specific structure, for the sake of simplicity.

As depicted in FIG. 4, NDE device 400 includes guide wheels 405, tension sensor 415, elongation or distance sensor 425, diametric sensor 435, health monitor 445 and data store 455. In operation, NDE device 400 obtains sensor data, such as from sensors 415, 425 and 435, associated with cordage product 460 while in-service handling an applied load. The sensor data may include any combination of applied load data, rope elongation data, and diametric data. In an embodiment, NDE device 400 may be configured to filter the obtained sensor data before or after analysis by health monitor 445 and/or storage in data store 455. Filtering the obtained sensor data may reduce measurement noise errors and/or increase fidelity of the sensor data.

Applied load data measures a tensile force exerted on cordage product 460 in an axial direction by the applied load. In an embodiment, applied load data may be obtained from a sensor that directly measures a tensile force exerted on cordage product 460, such as a tensiometer. For example, the applied load data may be directly obtained from tension sensor 415 within NDE device 400. In an embodiment, applied load data may be obtained from a sensor that indirectly measures a tensile force exerted on cordage product 460. For example, the applied load data may be indirectly obtained from a sensor that measures a load applied on a sheave or winch (not depicted) associated with cordage product 460.

Rope elongation data may be obtained from any indication of a change in distance between two or more known features of cordage product 460. In an embodiment, the two or more known features may include picks (e.g., pick 310 of FIG. 3), embedded detectable elements (e.g., conductive elements), external markings (e.g., marks 320 and 330 of FIG. 3), any other plurality of markings, or a combination thereof. In an embodiment, rope elongation data is obtained from elongation sensor 425, which may be implemented using any combination of a jockey wheel, a rotary encoder, image sensor, or other like structure.

In an embodiment, elongation sensor 425 may be further configured to measure a distance travelled in an axial direction by cordage product 460 while obtaining rope elongation data. In an embodiment, elongation sensor 425 may be further configured to measure a distance travelled by NDE device 400 relative to the cordage product 460 while obtaining rope elongation data. Such information about the distance travelled by cordage product 460 or NDE device 400 may be used to associate specific sensor data with particular locations of cordage product 460. Accordingly, information about such a distance travelled may facilitate localizing estimates of cordage product 460's current physical condition.

Diametric data is indicative of a change in a cross-sectional area of cordage product 460 as a tension force is exerted on cordage product 460. This cross-sectional area change may represent damage to cordage product 460 that results in a reduced number of fibers being present in particular sections of cordage product 460. Examples of such damage include abrasion, internal friction between fibers composing cordage product 460, cuts, shock loading, environmental exposure, chemical exposure, and the like. In an embodiment, diametric data may provide information about cordage product 460's physical dimensions in a radial direction, the radial direction being perpendicular to an axial direction of the cordage product. In an embodiment, diametric data is obtained from diametric sensor 435, which may be implemented using a profilometer, a spot laser gauge, an image sensor, and other like structure.

Health monitor 445 is generally configured to determine an axial stiffness value associated with cordage product 460 based on the sensor data that may include any combination of applied load data, rope elongation data, and diametric data. In an embodiment, the axial stiffness value is a measure of cordage product 460's ability to resist elongation while under a tensile load. In an embodiment, health monitor 445 may determine an axial stiffness value using sensor data representing multiple measurements associated with a particular section or point of cordage product 460. In this embodiment, an average of the sensor data may then be used in determining an axial stiffness value to help account for random variations (e.g., noise) in the sensor data that are not indicative of the measure data of interest.

NDE device 400 may also obtain reference data associated with a physical condition of cordage product 460. As an example, the reference data may include such data as an initial load-elongation curve for cordage product 460 that characterizes one or more tensile properties of cordage product 460 prior to being placed in-service. Reference data may also include historical sensor data associated with cordage product 460 previously obtained while cordage product 460 was in-service handling loads. In another example, reference data may include known information, such as polymer data providing information about one or more polymers composing cordage product 460. Examples of polymer data include information about cross-linking, degree of crystallinity, molecular weight, polymer scissions, modulus of elasticity, and the like.

In an embodiment, NDE device 400 obtains the reference data from data store 455 that provides NDE device 400 with data storage capabilities. Data store 455 may also provide NDE device 400 with data storage capabilities as sensor data is collected and as results are computed. In an embodiment, data store 455 receives applied load data from tension sensor 415, rope elongation data from elongation sensor 425, and diametric data from diametric sensor 435. In an embodiment, data store 455 stores metadata associated with sensor data. For example, metadata may include a timestamp associated with the sensor data, positional data correlating the sensor data to particular locations of cordage product 460, source identifying information, sampling intervals, sensor data type, and the like. In an embodiment, data store 455 is located remotely from the sensors 415, 425 and 435, but still forms a part of NDE device 400.

Health monitor 445 is further configured to generate a result that is an estimate of a health state of cordage product 460 using the determined axial stiffness value. In an embodiment, the result is generated in real time. In an embodiment, the result is generated some time (predetermined or otherwise) after the sensor data is collected. In an embodiment, the health monitor 455 is collocated with the sensors 415, 425 and 435. In an embodiment, the health monitor 455 is located remotely from the sensors 415, 425 and 435, but still forms a part of NDE device 400.

The estimated health state is indicative of the current physical condition of cordage product 460. Examples of a health state estimated by health monitor 445 for cordage product 460 include a residual strength, a current break point, a current modulus of elasticity, a yield load, and the like. In an embodiment, the estimated health state may be used by NDE device 400 to estimate a remaining service life of cordage product 460. In an embodiment, NDE device 400 may use the estimated health state to determine a likelihood that cordage product 460 will fail under one or more predefined conditions.

In an embodiment, health monitor 445 may perform a transform analysis when estimating a health state of cordage product 460. The transform analysis may include interpolating the sensor data to a time interval and extracting frequency characteristics from the interpolated sensor data. For example, when there is an adequate level of periodicity in the two or more known features, the health monitor 445 may use a Fast Fourier Transform to extract the frequency characteristics. In an embodiment, the health monitor 445 may use a frequency transform or other type of transform. By performing the transform analysis, health monitor 445 may be able to directly identify potential failure locations of cordage product 460. The transform analysis may also facilitate quantifying a severity of physical damage experienced by cordage product 460 while in-service.

In an embodiment, health monitor 445 may also consider reference data in addition to sensor data when estimating a health state of cordage product 460. For example, health monitor 445 may generate an expected stiffness value using the reference data. The expected stiffness value generated with the reference data may be compared to the determined stiffness value generated using the sensor data and that comparison may be used to generate the health estimate.

As another example, health monitor 445 may generate a current load-elongation curve using the sensor data. The current load-elongation curve may characterize various tensile properties of cordage product 460 when the sensor data was obtained. In estimating a health state of cordage product 460, health monitor may compare the current load-elongation curve with an initial load-elongation curve provided as reference data and that comparison may be used to generate the health estimate.

In comparing current load-elongation curves with the initial load-elongation curve, NDE device 400 may monitor a rate of change corresponding with one or more tensile properties associated with cordage product 460. Monitoring this rate of change may enable NDE device 400 to determine that cordage product 460 is failing if the rate of change exceeds a specified threshold within a predetermined period of time.

Figure 5:
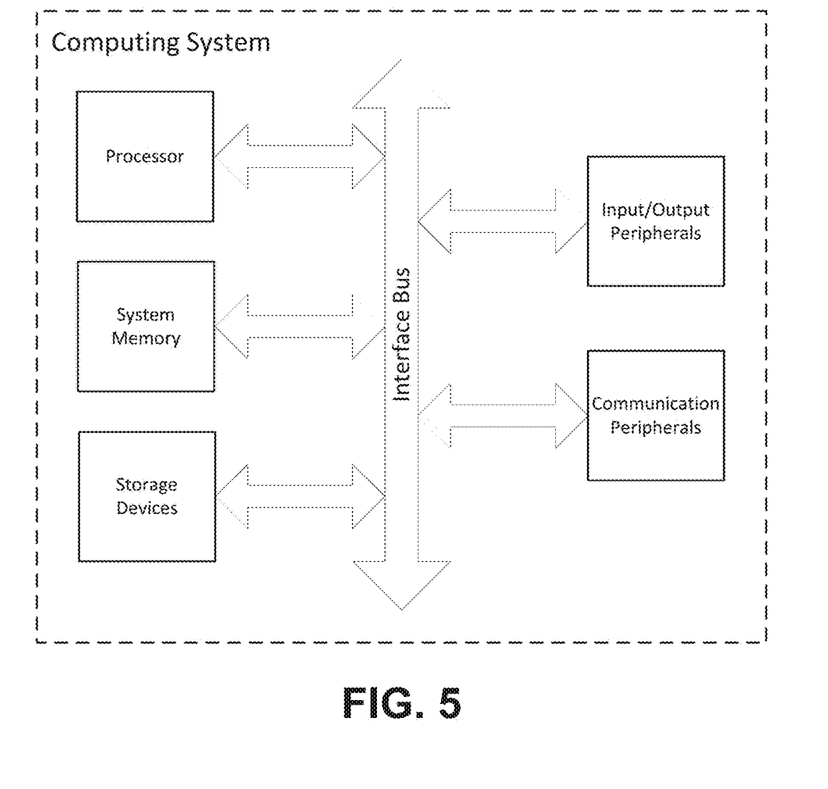
FIG. 5 is an illustration of an exemplary block diagram representing a general purpose computer system in which aspects of the methods and systems disclosed herein or portions thereof may be incorporated.

FIG. 5 is a block diagram of an example general purpose computing system in which embodiments of the invention, such as the health monitor 445 and data store 455 may be implemented. The computing system depicted by FIG. 5 may include hardware modules, software module, or a combination thereof that can be used to implement the disclosed health monitor 445. In a basic configuration, the computing system may include at least a processor, a system memory, a storage device, input/output peripherals, communication peripherals, and an interface bus. The input/output peripherals may be used, for example, to communicate with and control the sensors 415, 425 and 435. The communication peripherals may be used, for example, if the health monitor 445 and/or data store 455 are remotely located, or to report results of the health analysis to a remote system, such as a computer server, the computerized equipment in the cab of a crane, the computerized equipment on a ship, etc.

The interface bus is configured to communicate, transmit, and transfer data, controls, and commands between the various components of the electronic device. The system memory and the storage device comprise computer readable storage media, such as RAM, ROM, EEPROM, hard-drives, CD-ROMs, optical storage devices, magnetic storage devices, flash memory, and other tangible storage media. Any of such computer readable storage medium can be configured to store instructions or program codes embodying aspects of the disclosure. Additionally, the system memory comprises an operation system and applications. The processor is configured to execute the stored instructions and can comprise, for example, a logical processing unit, a microprocessor, a digital signal processor, and the like.

The system memory and the storage device may also comprise computer readable signal media. A computer readable signal medium may include a propagated data signal with computer readable program code embodied therein. Such a propagated signal may take any of variety of forms including, but not limited to, electro-magnetic, optical, or any combination thereof. A computer readable signal medium may be any computer readable medium that is not a computer readable storage medium and that can communicate, propagate, or transport a program for use in connection with the computing system.

Further, the input and output peripherals include user interfaces such as a keyboard, screen, microphone, speaker, other input/output devices, and computing components such as digital-to-analog and analog-to-digital converters, graphical processing units, serial ports, parallel ports, and universal serial bus. The input/output peripherals may also include a variety of sensors, such as tensiometers, spot laser gauges, jockey wheels, rotary encoders, topographic imaging devices, profilometer sensors, imaging sensors, as well as other types of sensors. The input/output peripherals may be connected to the processor through any of the ports coupled to the interface bus.

The user interfaces can be configured to allow a user of the computing system to interact with the computing system. For example, the computing system may include instructions that, when executed, cause the computing system to generate a user interface and carry out other methods and operations that the user can use to provide input to the computing system and to receive an output from the computing system.

Finally, the communication peripherals of the computing system are configured to facilitate communication between the computing system and other computing systems (e.g., between the computing device and a server) over a communications network. The communication peripherals include, for example, a network interface controller, modem, various modulators/demodulators and encoders/decoders, wireless and wired interface cards, antenna, and the like.

The communication network includes a network of any type that is suitable for providing communications between the computing device and the server and may comprise a combination of discrete networks which may use different technologies. For example, the communications network includes a cellular network, a WiFi/broadband network, a local area network (LAN), a wide area network (WAN), a telephony network, a fiber-optic network, or combinations thereof. In an example embodiment, the communication network includes the Internet and any networks adapted to communicate with the Internet. The communications network may be also configured as a means for transmitting data between the computing device and the other computing systems.

The techniques described above may be embodied in, and fully or partially automated by, code modules executed by one or more computers or computer processors. The code modules may be stored on any type of non-transitory computer-readable medium or computer storage device, such as hard drives, solid state memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage. Volatile and non-volatile storage, as used herein, excludes propagating or transitory signals per se.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only, and are not intended to limit the scope the disclosures herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the disclosures herein. The accompanying claims and their equivalents are intended to cover such forms or modifications as would fall within the scope and spirit of certain of the disclosures herein.

What is claimed:

1. A system for non-destructively estimating a current physical condition of a cordage product in-service, the system comprising:
    a distance sensor configured to provide cordage product elongation data indicative of a change in distance between two or more known features of the cordage product;
    a tension sensor configured to provide applied load data indicative of tension exerted on the cordage product in an axial direction while in-service; and
    a monitoring device coupled to the distance sensor and the tension sensor, the monitoring device configured to:
        obtain sensor data associated with the cordage product while in-service handling a load, the sensor data including one or more of the cordage product elongation data and the applied load data;
        determine an axial stiffness value associated with the cordage product based on the sensor data and independent of a known length of the cordage product; and
        estimate a health state of the cordage product based in part on the determined axial stiffness value, the health state indicative of the current physical condition of the cordage product.

2. The system of claim 1, further comprising a diametric sensor configured to provide diametric data indicative of a diameter of the cordage product perpendicular to the axial direction, and wherein the sensor data includes one or more of the cordage product elongation data, the applied load data, and the diametric data.

3. The system of claim 1, wherein the monitor device is further configured to obtain reference data associated with a physical condition of the cordage product, the reference data including one or more of: historical sensor data associated with the cordage product previously obtained while the cordage product was in-service handling loads, an initial load-elongation curve that characterizes various tensile properties of the cordage product, and at least one historical axial stiffness value determined using historical sensor data.

4. The system of claim 3, wherein the estimated health state is further based on the reference data.

5. A computer-implemented method for non-destructively estimating a current physical condition of a cordage product in-service, the method comprising;
    obtaining sensor data associated with the cordage product while in-service handling a load, the sensor data including one or more of: cordage product elongation data, applied load data, and diametric data;
    determining an axial stiffness value associated with the cordage product based on the sensor data and independent of a known length of the cordage product; and
    estimating a health state of the cordage product based on the determined axial stiffness value, the health state indicative of the current physical condition of the cordage product.

6. The computer-implemented method of claim 5, wherein the cordage product elongation data is indicative of a change in distance between two or more known features of the cordage product.

7. The computer-implemented method of claim 6, wherein the two or more known features include picks, embedded detectable elements, external markings, or a combination thereof.

8. The computer-implemented method of claim 5, wherein estimating the health state includes:
   interpolating the sensor data to a time interval; and
   extracting frequency characteristics from the interpolated sensor data using a transform.

9. The computer-implemented method of claim 5, wherein the cordage product is a fiber rope and wherein the estimated health state is a residual strength of the fiber of the fiber rope.

10. The computer-implemented method of claim 5, wherein the sensor data is obtained by one or more sensors over an entire length of the cordage product passing by the one or more sensor, and wherein determining the axial stiffness is limited to sensor data at discrete points or discrete sublengths along the entire length.

11. The computer-implemented method of claim 5, further comprising:
   filtering the sensor data to reduce measurement noise errors and increase fidelity.

12. The computer-implemented method of claim 5, wherein the sensor data is obtained by one or more sensors over a portion of the cordage product passing by the one or more sensor, wherein sensor data from the portion is obtained multiple times over a predetermined period of time, and further comprising determining if the health state exceeds a threshold for a rate of health decrease.

13. The computer-implemented method of claim 5, further comprising:
   utilizing the estimated health state to determine a likelihood that the cordage product will fail under one or more predefined conditions.

14. The computer-implemented method of claim 5, further comprising:
   utilizing the estimated health state to estimate a remaining service lifetime of the cordage product.

15. A computing system for non-destructively estimating a current physical condition of a cordage product in-service, the computing system comprising:
   one or more processors; and
   a memory communicatively coupled to the one or more processors, the memory bearing instructions that, when executed on the one or more processors, cause the computing system to at least:
     obtain reference data associated with a physical condition of the cordage product;
     obtain sensor data associated with the cordage product while in-service handling a load;
     determine an axial stiffness value associated with the cordage product based on the sensor data and independent of a known length of the cordage product; and
     estimate a health state of the cordage product based on the determined axial stiffness value and the obtained reference value, the health state indicative of the current physical condition of the cordage product.

16. The computing system of claim 15, wherein the reference data includes one or more of historical sensor data associated with the cordage product previously obtained while the cordage product was in-service handling loads, an initial load-elongation curve that characterizes various tensile properties of the cordage product, and at least one historical axial stiffness value determined using historical sensor data.

17. The computing system of claim 15, wherein the instructions further cause the computing system to compare the determined axial stiffness value to the reference data when estimating the health state of the cordage product.

18. The computing system of claim 15, wherein the instructions further cause the computing system to generate a current load-elongation curve based on the sensor data, the current load-elongation curve characterizing various tensile properties of the cordage product when the sensor data was obtained.

19. The computing system of claim 18, wherein the instructions further cause the computing system to compare the current load-elongation curve to the reference data when estimating the health state of the cordage product.

20. The computing system of claim 15, wherein the sensor data includes one or more of: cordage product elongation data, applied load data, and diametric data.

21. The computing system of claim 15, wherein the reference data further includes polymer data providing information about one or more polymers composing the cordage product.

22. The computing system of claim 21, wherein the polymer data includes information about cross-linking, degree of crystallinity, molecular weight, polymer scissions, modulus of elasticity, or a combination thereof.

* * * * *